United States Patent
Ferguson et al.

(10) Patent No.: US 7,129,491 B2
(45) Date of Patent: Oct. 31, 2006

(54) DIFFRACTION MODE TERAHERTZ TOMOGRAPHY

(75) Inventors: Bradley Ferguson, Northgate (AU); Shaohong Wang, Budd Lake, NY (US); Xi-Cheng Zhang, Melrose, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 342 days.

(21) Appl. No.: 10/843,899

(22) Filed: May 12, 2004

(65) Prior Publication Data

US 2005/0253071 A1    Nov. 17, 2005

Related U.S. Application Data

(63) Continuation-in-part of application No. PCT/US02/36279, filed on Nov. 13, 2002.

(51) Int. Cl.
*G01J 5/02* (2006.01)
(52) U.S. Cl. .................................. 250/341.1
(58) Field of Classification Search ........... 250/341.1
See application file for complete search history.

(56) References Cited

U.S. PATENT DOCUMENTS

| | | | |
|---|---|---|---|
| 4,594,662 A * | 6/1986 | Devaney | 700/90 |
| 5,710,430 A | 1/1998 | Nuss | |
| 5,789,750 A | 8/1998 | Nuss | |
| 5,939,721 A | 8/1999 | Jacobsen et al. | |
| 5,952,818 A | 9/1999 | Zhang et al. | |
| 6,078,047 A * | 6/2000 | Mittleman et al. | 250/338.1 |
| 6,414,473 B1 * | 7/2002 | Zhang et al. | 324/96 |
| 6,977,379 B1 * | 12/2005 | Zhang et al. | 250/341.1 |
| 2001/0029436 A1 | 10/2001 | Fukasawa | |
| 2004/0010196 A1 * | 1/2004 | Wang et al. | 600/476 |
| 2004/0130725 A1 * | 7/2004 | Kido et al. | 356/484 |
| 2005/0023470 A1 * | 2/2005 | Ferguson et al. | 250/358.1 |
| 2006/0055936 A1 * | 3/2006 | Yun et al. | 356/479 |

OTHER PUBLICATIONS

Mittleman et al., T-Ray Imaging, Sep. 1996, Quantum Electronics, vol. 2, pp. 678-692.*
Zhang, XC, T-Ray Computed Tomography, 2002, IEEE/LEOS, pp. 1-4.*
Fitzgerald et al, An Introduction to medical imaging with Coherent Terahertz Frequency Radiation, Mar. 2002, Phys.Med. Biol, vol. 47, pp. R67-R84.*
Recent advantages towards in-vivo THz Imaging and diagnosis—Presentation by B. Ferguson, S. Wang, D. Abbott and X.-C. Zhang—International Conference on Biomedical Imaging and Sensing Application with Terahertz Technology, Dec. 1, 2001.
X.-C. Zhang; T-Ray Computed Tomography; pp. 1-4; Hot Topic, IEEE/LEOS News Letters, 2002, USA.

(Continued)

*Primary Examiner*—David Porta
*Assistant Examiner*—Christine Sung
(74) *Attorney, Agent, or Firm*—RatnerPrestia (57) ABSTRACT

A method of obtaining a series of images of a three-dimensional object. The method includes the steps of transmitting pulsed terahertz (THz) radiation through the entire object from a plurality of angles, optically detecting changes in the transmitted THz radiation using pulsed laser radiation, and constructing a plurality of imaged slices of the three-dimensional object using the detected changes in the transmitted THz radiation. The THz radiation is transmitted through the object as a two-dimensional array of parallel rays. The optical detection is an array of detectors such as a CCD sensor.

23 Claims, 6 Drawing Sheets

OTHER PUBLICATIONS

Bradley Ferguson, Shaohong Wang, Doug Gray, Derek Abbot, X.-C. Zhang; T-Ray computed tomography; Optics Letters, vol. 27, No. 15, pp. 1312-1314; Aug. 1, 2002, Optical Society of America; USA.

Bradley Ferguson, Shaohong Wang, Doug Gray, Derek Abbott, X-C Zhang; Towards functional 3D T-ray imaging; Physics in Medicine and Biology; Phys. Med. Biol. 47 (2002); pp. 3735-3742; Institute of Physics Publishing; USA.

A. Boh Ruffin, Joan Decker, Laurent Sanchez-Palencia, Lenaic Le Hors, John F. Whitaker, Theodore B. Norris, J. V. Rudd; Time reversal and object reconstruction with single-cycle pulses; Optic Letters, vol. 26, No. 10; pp. 681-683; May 15, 2001; Optical Society of America; USA.

Zhiping Jiang, X.-C. Zhang; THz Imaging via Electro-Optic Effect; 1999 IEEE MTT-S Digest, pp. 941-944; IEEE; USA.

Peter M. Van Den Berg, Ralph E. Kleinman; A contrast source inversion method; Inverse Problems 13 (1997); pp. 1607-1620; IOP Publishing Ltd., UK.

Frank Natterer, Frank Wubbeling; Chapter 3.3: Diffraction Tomography, pp. 46-50; Chapter 5: Reconstruction Algorithms, pp. 81-83; Mathematical Methods in Image Reconstruction; USA.

Zhiping Jiang, X. G. Xu, X.-C. Zhang; Improvement of terahertz imaging with dynamic subtration technique; Applied Optics, vol. 39, No. 17, Jun. 10, 2000; pp. 2982-2987; Optical Society of America; USA.

Q. Wu, T.D. Hewitt, X.-C. Zhang; Two-dimensional electro-optic imaging of THz beams; Appl. Phys. Lett 69 (8), Aug. 19, 1996; pp. 1026-1028; American Institute of Physics; USA.

F.G. Sun, Zhiping Jiang, X.-C. Zhang; Analysis of terahertz pulse measurement with a chirped probe beam; Applied Physics Letters, vol. 73, No. 16, Oct. 19, 1998; pp. 2233-2235; American Institute of Physics; USA.

Zhiping Jiang, X.-C. Zhang; Electro-optic measurement of THz field pulses with a chirped optical beam; Applied Physics Letters, vol. 72, No. 16, Apr. 20, 1998; pp. 1945-1947; American Institute of Physics; USA.

Z. G. Lu, P. Campbell, X.-C. Zhang; Free-space electro-optic sampling with a high-repetition-rate regenerative amplified laser; Appl. Phys. Lett. 71 (5), Aug. 4, 1997; pp. 593-595; American Institute of Physics; USA.

Daniel M. Mittleman, Stefan Hunsche, Luc Boivin, Martin C. Nuss; T-ray tomography; Optic Letters, vol. 22, No. 12; Jun. 15, 1997; pp. 904-906.

Bradley Ferguson, Shaohong Wang, Douglas A. Gray, Derek Abbott, Xi-Cheng Zhang; Terahertz Imaging of biological tissue using a chirped probe pulse; Electronics and Structures for MEMS II; Proceedings of SPIE, vol. 4591; Nov. 2001; pp. 172-184.

A.C. Kak and Malcolm Slaney; Principles of Computerized Tomographic Imaging; Society of Industrial and Applied Mathematics; 2001; pp. 17-25.

Martin C. Nuss; Chemistry Is Right for T-Ray Imaging; IEEE Circuits & Devices; Mar. 1996; pp. 25-30.

Shiping Jiang and X.-C. Zhang, 2D Measurement and Spatio-Temporal Coupling of Few-Cycle THz Pulses; Optics Express, vol. 5, No. 11, Nov. 22, 1999, pp. 243-248.

* cited by examiner

DIFFRACTION MODE TERAHERTZ TOMOGRAPHY

This application is a continuation-in-part application of PCT International Application No. PCT/US02/36279 filed on Nov. 13, 2002 designating the United States, the entire contents of which are incorporated in this document by reference.

The U.S. Government has a paid-up license in this invention and the right in limited circumstances to require the patent owner to license others on reasonable terms as provided for by the terms of Contract No. DE-FG07-98ER6270 awarded by the Department of Energy and Contract Nos. DAAD-19-99-1-0333 and DAAD-1999C0045 awarded by the U.S. Army.

FIELD OF THE INVENTION

The invention relates generally to T-ray imaging and, more particularly, to techniques for obtaining and imaging three-dimensional objects using radiation in the terahertz (THz) spectrum.

BACKGROUND OF THE INVENTION

The term terahertz, originally used by sub-millimeter spectroscopists to describe spectral lines with frequencies in the trillions of hertz, today is applied to broadband pulsed electromagnetic (EM) radiation between the infrared and microwave bands of the EM spectrum, ranging from 0.1 to 10 THz. The photon energies of THz radiation range from 0.4 to 80 mev, which corresponds to the range of fundamental energies associated with changes between molecular energy levels.

Over the past 20 years the technologies in the THz field have developed significantly, both in the generation of THz radiation as well as in its detection. Recent advances in high-speed optoelectronic and femtosecond laser technology facilitate generation and detection of short bursts of terahertz radiation, which has been proven to be extremely useful for spectroscopic measurements in the sub-millimeter wave range. Terahertz imaging combines these coherent spectroscopic measurements with real-time imaging and advanced signal processing and recognition, so that each pixel element of the image contains spectroscopic information about the object. Terahertz radiation is described in greater detail in an article by M. Nuss entitled "Chemistry is Right for T-Ray Imaging," Circuits & Devices, IEEE (March, 1996).

Typical apparatus and associated imaging methods for free-space electro-optic characterization of propagating terahertz beams are described in U.S. Pat. No. 5,952,818 issued on Sep. 14, 1999 to Zhang et al. and assigned to the assignee of the present invention, Rensselaer Polytechnic Institute. The sensing technique is based on a non-linear coupling between a low-frequency electric field (terahertz pulse) and a laser beam (optical pulse) in an electro-optic crystal, such as a zinc telluride (ZnTe) crystal. Modulating the crystal's birefringence by applying the polarized electric field to the crystal modulates the polarization states of an optical probe beam passing through the crystal. This ellipticity modulation of the optical beam is then polarization-analyzed to provide information on both the amplitude and phase of the applied electric field.

A further improvement in terahertz imaging is disclosed in U.S. Pat. No. 6,414,473 issued on Jul. 2, 2002 to Zhang et al and also assigned to Rensselaer Polytechnic Institute. The described imaging system in this reference employs a chirped optical beam and dynamic subtraction to rapidly reconstruct an image thereby providing a system that is suitable for real-time imaging applications. According to this patent, the imaging system generates a free-space electromagnetic radiation pulse that can be positioned to pass through the object to be imaged, and one of an electro-optic crystal or a magneto-optic crystal positioned so that the electromagnetic radiation pulse passes through the crystal after passing through the object.

The system further generates a chirped optical probe signal to impinge the crystal simultaneously with the electromagnetic radiation pulse passing through the crystal so that a temporal waveform of the radiation is encoded onto a wavelength spectrum of the chirped optical probe signal. The chirped optical probe signal modulated by the free-space radiation is then passed to a decoder for decoding a characteristic of the free-space electromagnetic radiation using the chirped optical probe signal with the temporal waveform of the radiation encoded on the signal. The system further determines a characteristic of the object using the characterization of the free-space electromagnetic radiation pulse after passing through the object.

The use of a chirped optical probe increases the speed of data acquisition and greatly enhances the utility of terahertz computed tomography (THz-CT) technology. Image acquisition time remains comparatively long, however, due to the requirement that a target be scanned point-by-point to obtain the information necessary to reconstruct a target image.

It would be highly desirable, therefore, to develop a system that permits irradiating the full sample cross section at a given incidence angle with THz radiation and detecting the emerging THz radiation for the full target cross section rather than scanning the target point-by-point. Efforts to do so by expanding the THz beam have unfortunately been hampered by a number of problems, including poor signal-to-noise ratios (SNR) and quality of image reconstruction. A need remains to provide such as system.

SUMMARY OF THE INVENTION

In one aspect, the invention includes a system for performing T-ray imaging. The system simultaneously provides a THz pulse and an optical pulse; directs the THz pulse in a first path through an object; and directs the optical pulse through a second path not through the object. An electro-optic crystal, located at a point of conversion of the first path and second path, provides modulation of the optical pulse with the THz pulse to create a modulated optical pulse. The system also detects the modulated optical pulse and stores information relating to the detected modulated optical pulse.

In one embodiment, the system may rotate the object relative to the THz pulse propagation to obtain the plurality of projection angles. In such an embodiment, the object may be physically rotated or the mechanism that provides the THz pulse may be physically rotated. In another embodiment, the THz pulse may be transmitted from a plurality of projection angles simultaneously, with a corresponding detector provided for each of the projection angles. Finally, the system constructs a three-dimensional image of the object using the information obtained for the plurality of pixels for the plurality of projection angles.

The system according to the present invention may comprise:

a. an optical probe beam path and a pulsed optical probe beam generator;

b. a THz beam path and a pulsed THz radiation beam generator;

c. a two-dimensional THz radiation sensor;
d. a sample holding area;
e. a two-dimensional optical sensor; and
f. a mechanism for converging both the THz path and the optical beam path onto the THz sensor, wherein:

the optical probe beam generator generates an expanded collimated optical probe beam traveling along the optical probe beam path;

the THz beam generator generates an expanded and collimated THz beam traveling along the THz Beam path;

the sample holding area is in the THz beam path and is adapted to permit changing an orientation of a sample placed in the path relative to the THz beam;

the two-dimensional THz radiation sensor has an area $A_s$ and is positioned along the THz beam path at a distance from the sample such that area $A_s$ intercepts all THz radiation emerging from the sample along the THz path within a divergence angle of about 12 degrees or more; and the expanded optical probe beam has a cross section larger than a cross section of the THz beam incident on the THz sensor, and the optical sensor is positioned along the optical beam path and has an area larger than the cross section of the expanded optical probe beam.

The mechanism for detecting the modulated optical pulse may comprise a two-dimensional charged coupled device (CCD) imaging system or a photoconductive antenna or an array of such antennas.

In another aspect, the present invention comprises a method of obtaining a series of images of a three-dimensional object by transmitting expanded pulsed THz radiation through an entire object from a plurality of angles, optically detecting changes in the transmitted THz radiation using pulsed laser radiation, and constructing a plurality of imaged slices of the three-dimensional object using the detected changes in the transmitted THz radiation. The THz radiation is transmitted through the object as a two-dimensional array of parallel rays and impinged onto a two-dimensional electro-optical sensor having an area $A_s$ and positioned along the THz beam path at a distance from the sample such that area $A_s$ intercepts all THz radiation emerging from the sample along the THz path within a divergence angle of about 12 degrees or more. The expanded optical probe beam has a cross section larger than a cross section of the THz beam incident on the THz sensor, and the optical sensor is positioned along the optical beam path and has an area larger than the cross section of the expanded optical probe beam. The optical detector is, typically, a two-dimensional array of detectors such as a CCD sensor.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

The invention will next be described with reference to the figures in which the same numbers are used to indicate the same elements in all figures. The figures are used to illustrate the invention and avoid elements not needed to explain the invention, so as not to unduly clutter and complicate the illustrations.

Figure 1A:
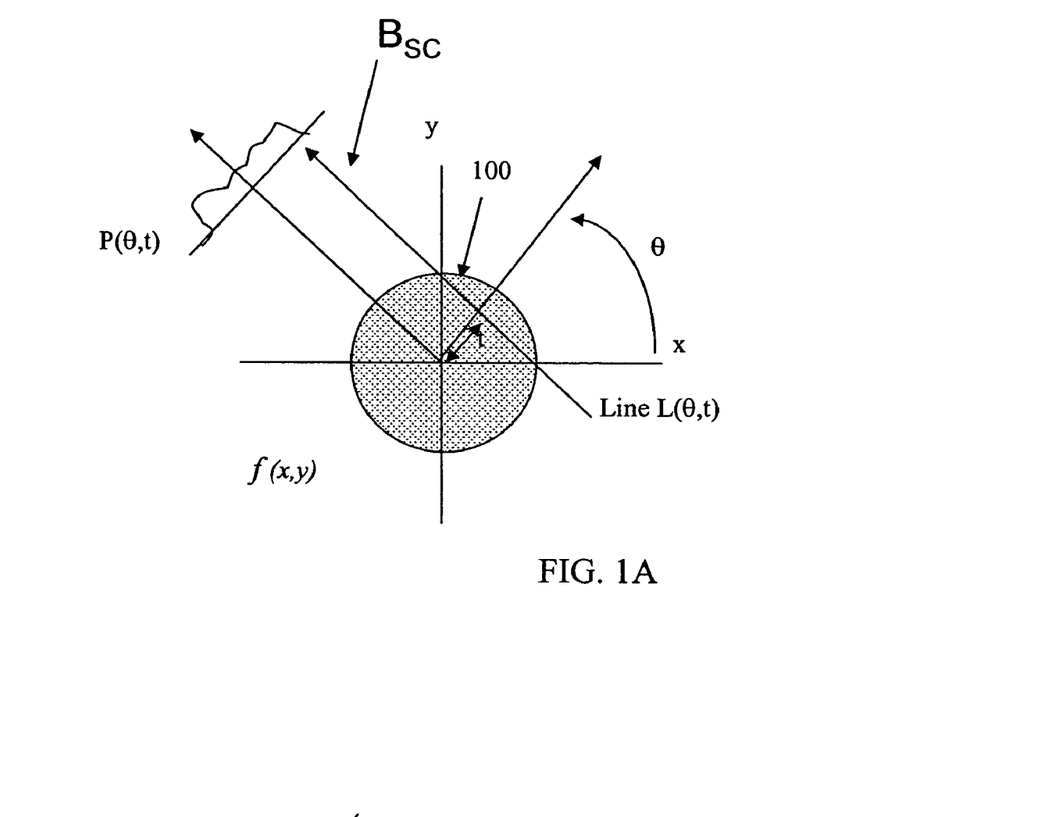
FIG. 1A is a schematic representation of the relative positions of a sample and the THz radiation and associated detector for examining the sample in computed tomography.

FIG. 1 illustrates the fundamental concept of THz CT. A sample 100 (the object) is scanned with THz radiation in the x-y plane in the direction of line L. When a T-ray is propagated through the sample, its attenuation, or object projection $P(\theta,t)$, is the line integral of the object function $f(x,y)$ along the line L, which is determined by the line orientation angle, $\theta$, and the offset, t, from the object origin. The object projection can be obtained by measuring the signal at various $\theta$ and t via rotating the sample. In the alternative, the radiation source and detector may be rotated while the sample remains stationary. This process is repeated to generate imaging data (including a temporal THz profile) for a number of projection angles $\theta$.

Figure 1B:
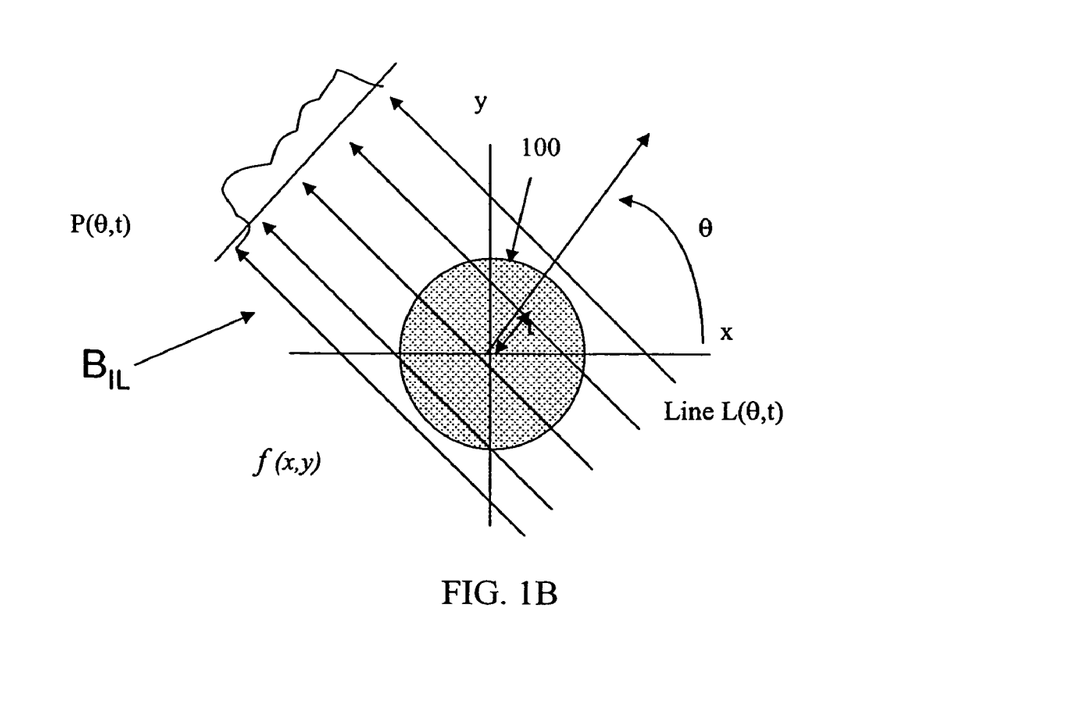
FIG. 1B is a schematic representation of the relative positions of a sample and the THz radiation and associated detector for examining the sample in diffraction tomography (THz-DT) according to the present invention.

T-ray diffraction tomography (THz-DT) differs from THz-CT in that instead of scanning a target with radiation focused to a single spot, the THz radiation is expanded to illuminate the full target at once. FIG. 1B illustrates how THz DT differs conceptually from the THz CT shown in FIG. 1A. In FIG. 1B, the sample 100 is not scanned by a focused THz beam, but is instead fully illuminated by an expanded THz beam ($B_{IL}$) again traveling along line L. Both techniques employ the pump-probe principle to develop imaging data.

Figure 2:
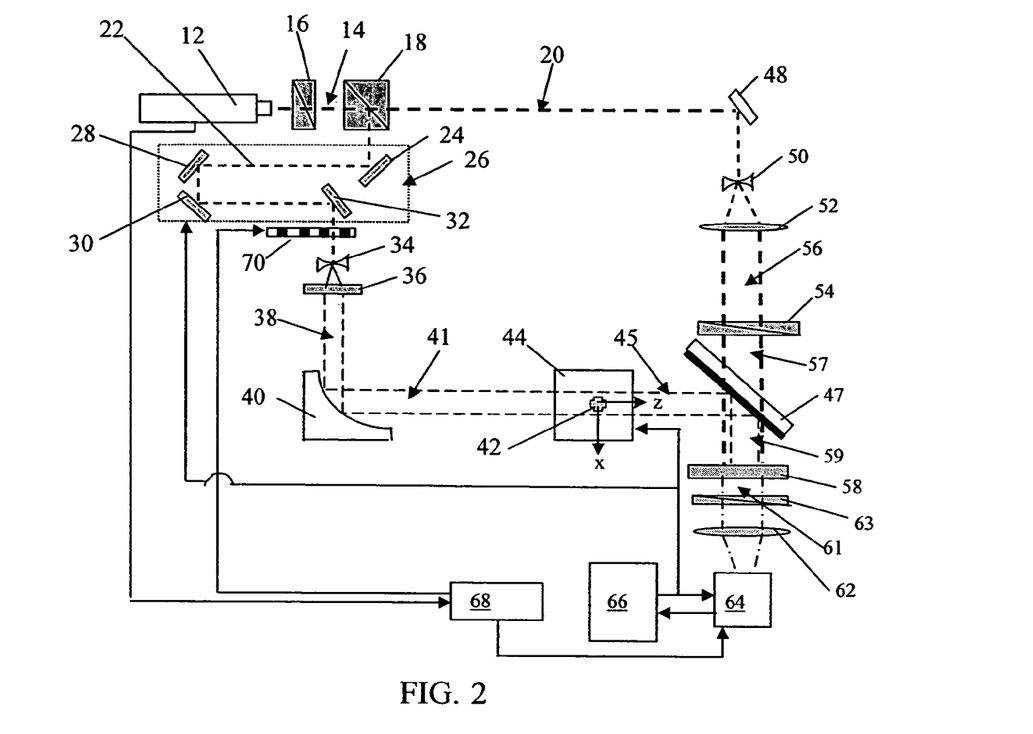
FIG. 2 is a schematic representation of a system useful in implementing THz-DT in accordance with this invention.

FIG. 2 illustrates a system for performing diffraction tomography in accordance with the present invention. This system includes a femtosecond laser unit 12, a planar THz beam generator 36, a two-dimensional THz sensor 58, and a sample position stage 44. Preferably, the stage 44 allows the sample 100 to be rotated around and translated along the x- or z-axis by a position controlling system such as, for example, one consisting of a rotational and two linear translational motors attached to stage 44. (Such a position controlling system is not illustrated in FIG. 2 to prevent unduly cluttering the figure.)

In one exemplary system, the laser unit 12 comprises a femtosecond (fs) laser such as a Mai Tai Mode-locked Ti:Sapphire laser and a Hurricane Ti:Sapphire regenerative Amplifier (made by Spectra-Physics Inc.). This laser is capable of generating 800 nm pulses with duration of 130 fs. The pulse energy and repetition rate are 700 µJ and 1 kHz, respectively.

The laser beam 14 from the laser unit 12 is split into a pump beam 22 and a probe beam 20 via, preferably, a polarizing cubic beam splitter 18. The system preferably further includes a half-wave plate 16 which may be rotated to adjust the intensity ratio between the pump beam 22 and the probe beam 20.

The pump beam 22 next transits a delay stage 26 comprising a combination of reflecting elements typically front surface mirrors. In the present exemplary embodiment, the delay stage 26 is shown as comprising mirrors 24, 28, 30, and 32. The optical path length between the entry and exit points of the pump beam 22 through the delay stage 26 is adjustable. Although four mirrors are shown in the present illustration, the number of mirrors used is not essential and fewer or more may be used depending, in part, on where one desires to direct the exiting radiation.

Following exit from the delay stage 26, the pulsed pump beam 22 is expanded by a negative lens 34 and impinged onto the THz beam generator 36. Again in an exemplary embodiment, the THz beam generator 36 may be a ZnTe electro-optic (EO) crystal, and the THz beam is generated via an optical rectification mechanism. The generated THz radiation beam 38 is next collimated and impinged onto a target. Again in the exemplary embodiment of FIG. 2, collimation is obtained with a 90 degree, off-axis, parabolic mirror 40. As more clearly shown in FIG. 4, the collimated THz beam 41 illuminates the target 42 placed on the stage 44. The interaction of the beam 41 and the target 42 results in a scattered emerging beam 45 on the other side of the target 42.

The optical probe beam 20 is also expanded and collimated to form an expanded Gaussian collimated optical probe beam 56. In the exemplary system shown in FIG. 2, this is accomplished by a system of mirrors generally represented by mirror 48, used to direct the optical probe beam 20 along a desired path, and a telescope beam expander consisting of a negative lens 50 followed by a positive lens 52. Expanded optical probe beam 56 is transmitted through a polarizing crystal 54 and emerges as a linearly polarized beam 57.

The polarized pulsed optical probe beam 57 and the pulsed THz beam 45 exiting the sample 42 are then directed along a coincident path and propagate co-linearly as combined beams 59. In a preferred embodiment, a tin-doped indium dioxide THz mirror 47 is used to combine the paths of the scattered THz emerging beam 45 and the polarized optical beam 57. The combined beams 59 and the scattered THz emerging beam 45 propagate co-linearly and impinge on sensor 58.

The probe beam and the THz pulse propagate through the ZnTe crystal at the same speed providing a measurement of the instantaneous THz field at the instant the probe pulse reaches the THz detector. The polarization of the probe beam is measured by passing it through a linear analyzer 63. The amplitude of the probe beam after the analyzer 63 is dependent upon its polarization, which in turn is dependent upon the THz field amplitude.

The sensor 58 is, preferably, an electro-optic crystal (such as ZnTe). The birefringence of the crystal is dependent upon the incident electric field. The polarization of the probe beam exiting the crystal is dependent upon the THz amplitude on the crystal at the time. Because this is a spatial effect, that is the birefringence of the crystal at any point is dependent on the THz amplitude at the same point, the two-dimensional polarization profile of the probe beam emerging from the sensor 58 matches the two-dimensional profile of the two-dimensional spatial THz electric field amplitude distribution on the sensor 58.

In other words, due to this electro-optical effect, the polarization of the probe beam is modulated by the THz two-dimensional diffraction pattern carried by the THz scattered radiation beam and the THz diffraction pattern is encoded onto the probe beam. Thus, T-ray diffraction tomography measures the two-dimensional spatial THz beam profile over the THz sensor simultaneously (in contrast to THz-CT which measures the THz field at a single point focused on the sensor, and scans the full cross sectional area of the target to obtain the same information).

The amplitude of the optical probe beam pulse 61 emerging from the sensor 58 representing the THz pulse amplitude (as a function of position) may be measured using an optical system comprising the analyzer 63, a focusing lens system 62, and a two-dimensional optical detector 64. In the exemplary system of FIG. 2, the optical detector 64 may be a CCD camera, such as an EEV 576×384, made by Princeton Instruments, Inc. The detection technique achieved by the exemplary system is referred to as two-dimensional free space electro-optic sampling (FSEOS).

Figure 4:
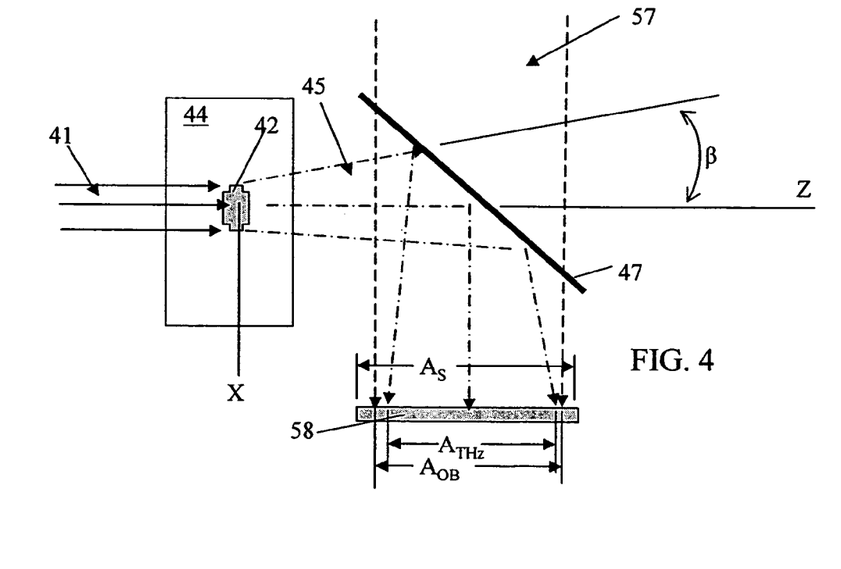
FIG. 4 is an enlarged portion of the system illustrated in FIG. 2 showing the relative positioning and sizes of the elements used in capturing THz radiation in accordance with this invention.

As best shown in FIG. 4, the sensor 58 has an effective area $A_s$ larger than the expanded optical probe beam 56 cross-sectional area $A_{OB}$, which is the same as the cross-sectional area of the polarized beam 57 and which again is larger than the THz beam 45 cross sectional area $A_{THz}$ incident on the sensor 58, as will be described below.

In a preferred embodiment, the SNR of the system may be improved through the use of a multi-channel, lock-in amplifier. In the alternative, two-dimensional THz measurements with good contrast and high SNR are possible using the synchronized dynamic subtraction measurement technique. See Z. Jiang and X.-C. Zhang, "Two dimensional measurements and spatio-temporal coupling of few-cycle terahertz pulses," Opt. Express 5, 243 (1999). Dynamic subtraction suppresses the phase uncertainties among the laser pulses, chopper trigger pulses (CTP), and CCD image acquisition trigger pulses (CIATP) in the two-dimensional THz measurement by controlling the phase of the chopper trigger pulses and the CCD image acquisition trigger pulses.

Referring again to FIG. 2, dynamic subtraction is implemented using a computer 66, a synchronizer 68 to provide a synchronizing signal to the optical detector 64 and the optical chopper 70. The laser output pulses are used as a reference clock input to the synchronizer 68. The synchronizer 68 generates CTP for the optical chopper 70 and CIATP. The frequency of the CIATP is exactly twice that of the CTP. Using the laser pulses as a reference clock to synchronize the CTP and CIATP achieves a phase-sensitive measurement equivalent to a multi-channel lock-in.

Figure 3:
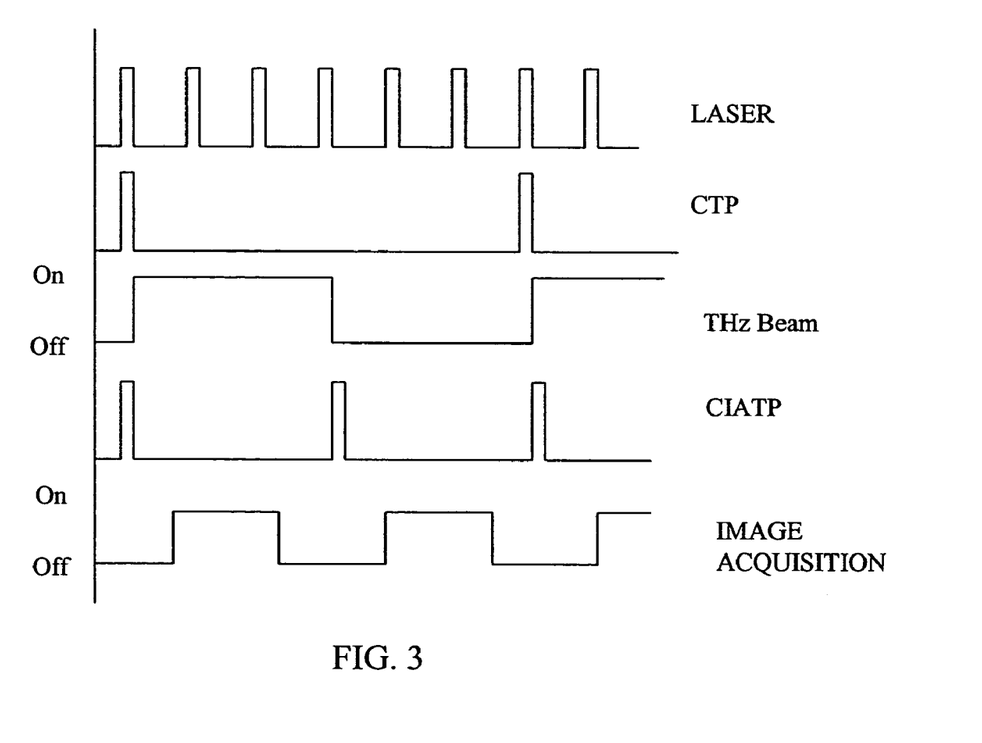
FIG. 3 illustrates the pulse sequence for implementing dynamic subtraction according to one aspect of this invention.

The THz beam on-off sequence and the CCD image acquisition sequence are shown in FIG. 3. In each chopper rotating period, the optical chopper 70 turns the pump beam on and off with 50% duty cycle, i.e., the THz beam is on for the same amount of time as it is off. During this period, the CCD camera takes two frame images: one corresponds to the image when the THz beam is on and the other corresponds to the image when the beam is off. The computer 66 subtracts one image from the other and then outputs the resulting image. This THz image measurement repeats N times with the final image result being the mean of the N measurements.

The entire image procedure can be expressed as:

$$U_{dynamic} \sim DFT[U(t)]_{f=f_0/2}$$

where $f_o$ is the image acquisition frequency, which is the inverse of the image acquisition period ($\delta t$); DFT denotes the discrete Fourier transformation. The acquisition frequency can be written as $f_0 = 1/\delta t$, which is smaller than the repetition rate of the laser pulses. The measurement represented in the above equation picks out the signal component that is modulated at a frequency $f=f_0/2$. This measurement is the same as the one measured using a multi-channel, lock-in amplifier with the same reference frequency of $f=f_0/2$. Using the synchronized dynamic subtraction two-dimensional THz measurement, the SNR of the THz DT imaging measurement was increased from a level of about 20 to about 120.

As stated earlier, the pump beam is reflected by mirrors 24, 28, 30, and 32 mounted on a translation stage forming a delay stage 26. This translation stage allows the path length of the pump beam to be modified. When the pump beam path is shortened, the THz pulse reaches the THz detector slightly before the probe beam pulse. The probe beam then measures the THz field at a slightly later time. This process is repeated many (i.e., hundreds of) times to allow the THz pulse temporal profile to be measured. This time domain THz pulse may be numerically Fourier transformed to calculate the frequency domain THz amplitude and phase, using the THz temporal pulse profile measured at each pixel of the CCD camera.

The THz pulse is diffracted as it propagates through the sample so the measured data corresponds to the diffraction pattern generated by the target. It is therefore important to capture this diffraction pattern.

One important aspect of this invention is the capture of THz radiation scattered by a sample placed in the sample holder. Due to the limited size of practical sensor crystals, this imposes a limit on the maximum distance from the sample to the sensor. It is contemplated that a practical method for capturing sufficient scattered radiation to permit reconstruction of the sample image will comprise capturing the scattered THz radiation emerging from the sample within at least a divergence angle $\beta$ equal to about 12 degrees, as shown in FIG. 4. In addition, the sensor is placed in what is known as the optical "far field," which means placing the sensor at a distance greater than about 20 THz wavelengths from the sample. Image reconstruction algorithms based on the Helmholtz equation or the Fresnel-Kirchhoff algorithms may then be used to reconstruct the target.

Capturing the diffraction pattern sufficiently to permit image reconstruction requires that the sensor 58 be positioned as close as possible to the target 42 to maximize the angular range over which the diffracted radiation is collected. Alternatively, several measurements may be made by sequentially placing the detector at different angles relative to the target.

Figure 5:
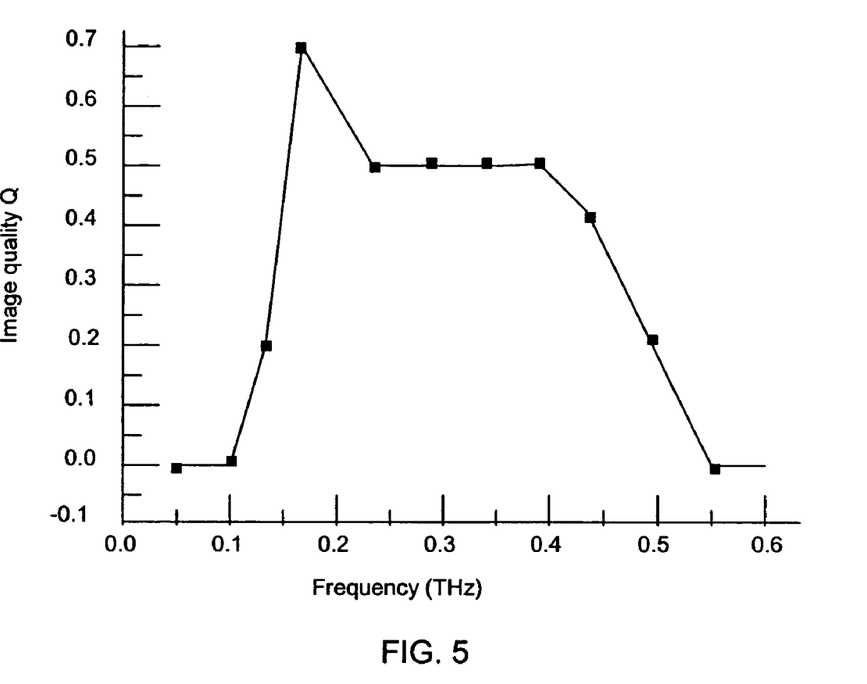
FIG. 5 shows the image quality of the reconstructed image in arbitrary units as a function of THz radiation frequency.
Figure 6:
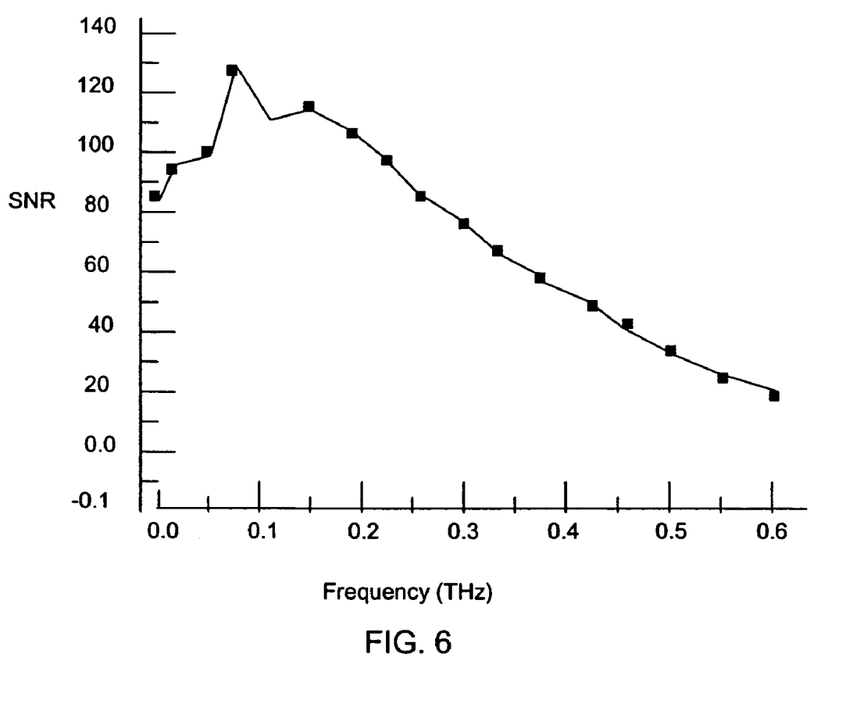
FIG. 6 shows the SNR as a function of THz radiation frequency.

The selected THz frequency affects the image quality of the reconstructed image, as well as the SNR. The data for the image quality, Q, of the THz DT at various frequencies for one source of THz radiation are shown in FIG. 5, which represents a particular implementation of this invention. The SNR data are shown in FIG. 6. As the THz frequency increases, the reconstructed image quality initially increases and then decreases with the THz frequency. For the THz frequencies of 0 to 0.2 THz, the better image quality at higher frequencies is due to the broadening spatial frequency bandwidth of the imaging system. In this instance, for the THz frequencies higher than 0.4 THz, poor SNR of the THz measurement degrades the image quality. Thus, a limiting frequency range for this source would be between about 0.1 and 0.5 THz; a preferred range would be between about 0.2 and 0.4 THZ; and a most preferred frequency would be between about 0.15 and 0.25 THz.

In accordance with the present invention, THZ frequency selection and the physical dimensions of the radiation beam cross sections and sensor area (better illustrated in FIG. 3) permit the use of standard diffraction tomography algorithms to reconstruct a sample by observing the following positioning restrictions:

(a) the effective sensor area $A_s$ and the area of the optical probe beam $A_{OB}$ incident on the sensor are large enough and/or close enough to the sample to capture the diffracted radiation over a significant diffraction angle, $\beta$, such angle being no less than about 12 degrees;

(b) the distance between the target 42 and the sensor 58 should be greater than 20 THZ wavelengths; and (c) an optimum THZ frequency, for the particular THz source used, is selected by determining the optimum compromise between SNR and image quality as a function of THz frequency.

FIGS. 2 and 4 show a system with a plurality of optical elements whose selection is a matter of directing beams along paths determined by the particular geometric requirements of the space and equipment available. Therefore, although the systems are shown schematically with a number of flat mirrors and beam splitters to create a logical schematic diagram, it should be understood that an actual system may have more or fewer mirrors and splitters, if any, as needed to fit the geometry of a particular workspace.

In operation, to obtain the data representing an image, an expanded THz pulse and an expanded optical probe pulse are transmitted along first and second paths. The THz radiation pulse is transmitted along a path that includes a sample holder where a target sample may be placed. When a target is placed on the sample holder, the THz pulse illuminates the sample. Preferably, the expanded THz beam fully illuminates the sample, meaning that the sample cross section in the beam path is smaller than the THz beam cross section. The two paths are combined and impinged on a sensor selected to spatially modulate the amplitude of the optical probe pulse as a function of the THz beam spatial intensity distribution on the sensor.

The spatially modulated expanded optical pulse is then detected, with a CCD camera comprising a two-dimensional array of optical sensors adapted to provide pixel information representing the spatially modulated pulse. This pixel-by-pixel information is stored typically in a memory. This process is performed with a sample in the sample holder and with the sample holder empty to provide a reference level. The reference level is then subtracted from the information obtained with the sample in place. A two-dimensional profile image of the object is then constructed using a mathematical algorithm based upon the time-reversal of the Huygen-Fresnel diffraction integral.

The T-ray DT system described in this document allows measurement of the diffraction pattern caused by a target. In addition to allowing three-dimensional reconstruction of the target using a plurality of projection angles, a two-dimensional profile may be reconstructed using the data from a single projection angle. A time-reversal of the Huygen-Fresnel diffraction integral may be used.

The use of this algorithm with the T-ray DT system is advantageous because it allows such a profile to be created using only a single pulse measurement, whereas previous uses of this algorithm for object reconstruction, as detailed by Ruffin et al. in "Time reversal and object reconstruction with single-cycle pulses," *Optics Letters*, 26(1), 681–683 (2001), required multiple pulses. Furthermore, this method permits a two-dimensional profile to be reconstructed despite having only a fairly limited view angle to collect the diffracted pattern. This method may also be used as the basis for a three-dimensional reconstruction technique.

In order to reconstruct the three-dimensional image of the sample, the generation, transmission, modulation, and detection of the THz and optical probe pulses are repeated for a plurality of projection angles relative to the object collectively representing a 360 degree revolution of the object. The reconstruction step comprises selecting and using a mathematical algorithm based on a linearization of the wave equation, such as a Born or Rytov approximation; an algorithm that inverts the non-linear wave equation using iterative finite difference techniques, such as a PBP algorithm; an iterative technique such as the Contrast Source Inversion method discussed by P. van den Berg and R. E. Kleinman, "A contrast source inversion method," *Inverse Problems*, 13, pp. 1607–1620 (1997), which is incorporated in this document by reference; or an algorithm based upon reconstruction of two-dimensional profiles of the object using Fresnel diffraction.

In addition, a doctorate thesis by S. Wang entitled "Three-Dimensional Terahertz Imaging," dated July 2003, and located at the Rensselaer Polytechnic Institute library in Troy, New York includes, among other information, mathematical algorithms appropriate for reconstructing an image using two-dimensional data obtained with a system such as illustrated in FIG. 2. This thesis is incorporated in this document in its entirety. Copies of the most pertinent pages are appended hereto as Appendix A.

EXAMPLE

The following example is included to more clearly demonstrate the overall nature of the invention. This example is exemplary, not restrictive, of the invention.

Figure 7:
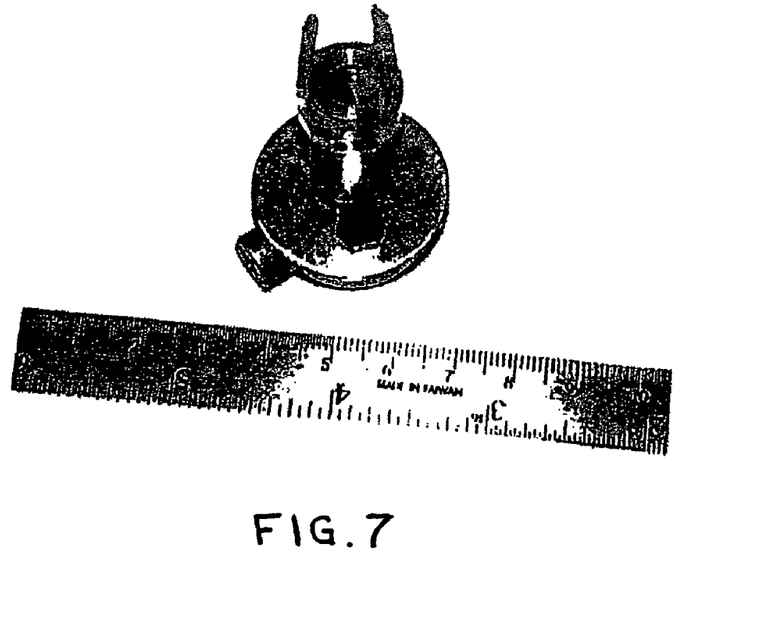
FIG. 7 shows a sample used to demonstrate THz-DT imaging.

An object composed of three, rectangular, polyethylene cylinders shown in FIG. 7 was used as a sample in an imaging system similar to the system shown in FIG. 2. The three cylinders were arranged in a triangle and each cylinder had a width of approximately 2 mm. The cylinders had a constant cross section that did not vary with height.

A GaAs photo-conductive antenna was used to generate the THz wave, which had a large amount of lower frequency components. The GaAs antenna gap was 15 mm. The image was acquired with a CCD camera using binning to improve the SNR. The dimensions of the image frame in pixels were 107×107. One hundred CCD frames were averaged at each time delay, again to improve the SNR.

Image reconstruction was done using both the first Born approximation and the Rytov approximation. In using the first Born approximation, the scattered wave was directly used to reconstruct the target. The scattered wave is:

$$U_s = u_m - u_0 \quad (1).$$

where $u_0$ is the incident THz wave without the sample, and $u_m$ is the measured THz wave with the sample present.

Using the first Rytov approximation, the following term is used to reconstruct the image of a target:

$$U_b = U_0 ln([u_s/u_0]+1) \quad (2).$$

Figure 8:
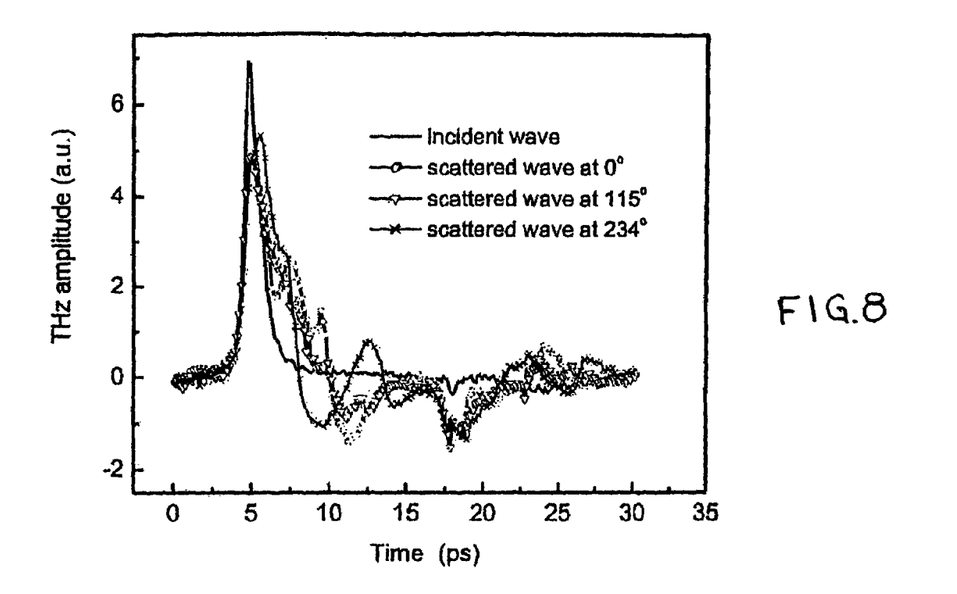
FIG. 8 shows the temporal THz signal amplitude obtained for the sample shown in FIG. 7.

The THz diffraction patterns were measured by rotating the target to different projection angles. FIG. 8 shows the THz waveforms measured at the center of the ZnTe sensor for three different projection angles. Due to the scattering, the THz waveforms show a high electric field at the time delay after the main incident peak. According to equation (1) above, the scattered wavelet component $u_s$ can be obtained by subtracting the incident waveform from the waveforms with the target present.

Figure 9:
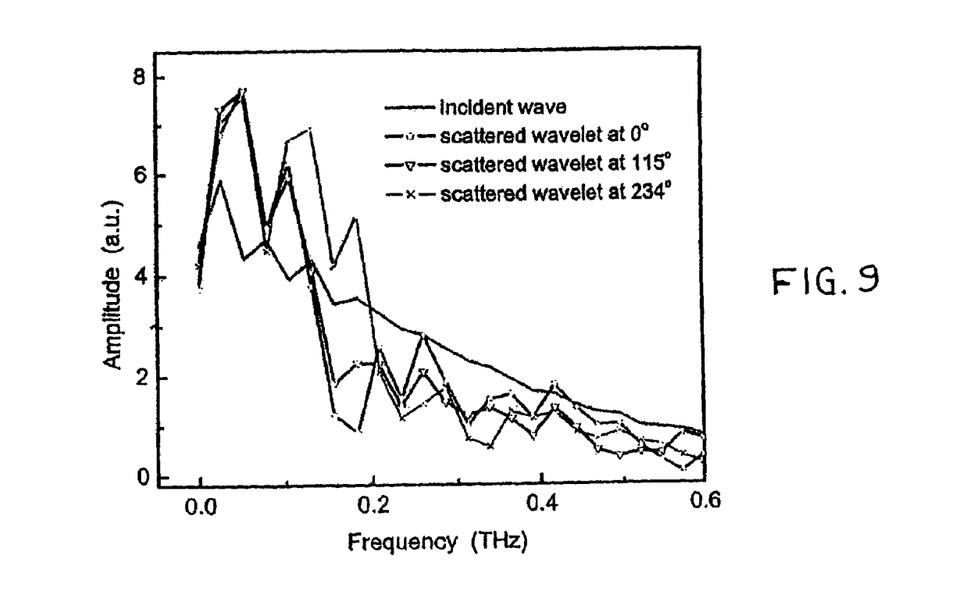
FIG. 9 shows the Fourier transform in the frequency domain of the data in FIG. 8.

Because the scattering process strongly depends on the incident wave frequency, picking out a frequency to perform the initial reconstruction for THz-DT experiment is very important to initialize the reconstruction algorithm. Such frequency was picked by obtaining the Fourier transformation of FIG. 8. The result is shown in FIG. 9. From FIG. 9, it is clear that the significant diffraction or scattering happens in the frequency range below 0.5 THz.

Figure 10:
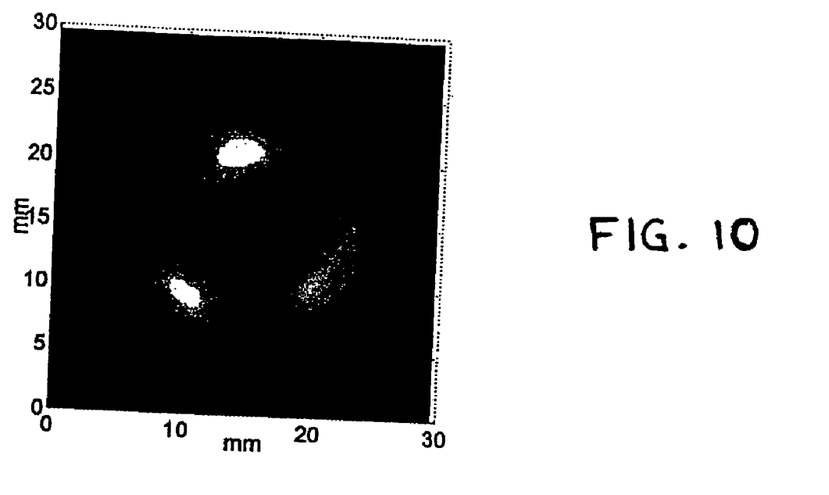
FIG. 10 shows a two-dimensional reconstruction of a section through the sample of FIG. 7.

For this polyethylene sample, the first Rytov approximation provided a better reconstruction. For this reconstruction, the frequency component of 0.2 THz was selected. The reconstruction result using the first Rytov approximation is shown in FIG. 10.

The invention has been described using a particular system set up with a combination of several specifically identified optical and mechanical elements. The invention is not limited to the specific elements used in the description, however, but encompasses any and all alternatives and substitutes that may be or become available, so long as the relationships among beam sizes, detector size, and positioning are maintained. Furthermore, the method is not limited to use only with EO crystals. Other sensors may be used, as, for example, photoconductive dipole antenna (PDA) arrays.

More generally, although the invention is illustrated and described above with reference to specific embodiments, the invention is not intended to be limited to the details shown. Rather, various modifications may be made in the details within the scope and range of equivalents of the claims and without departing from the invention.

What is claimed is:

1. A system for performing terahertz (THz) wave diffraction tomography, the system comprising:
   a. an optical probe beam path and a pulsed optical probe beam generator;
   b. a THz beam path and a pulsed THz radiation beam generator;
   c. a two-dimensional THz radiation sensor;
   d. a sample holding area;
   e. a two-dimensional optical sensor; and
   f. means for converging both the THz path and the optical beam path onto the THz sensor,
   wherein:
   the optical probe beam generator generates an expanded collimated optical probe beam traveling along the optical probe beam path;
   the THz beam generator generates an expanded and collimated THz beam traveling along the THz beam path;
   the sample holding area is in the THz beam path and is adapted to permit changing an orientation of a sample placed therein relative to the THz beam;
   the two-dimensional THz radiation sensor has an area $A_s$ and is positioned along the THz beam path at a distance from the sample such that area $A_s$ intercepts all THz radiation emerging from the sample along the THz path within a divergence angle of about 12 degrees or more; and the expanded optical probe beam has a cross section larger than a cross section of the THz beam incident on the THz sensor and the optical sensor is positioned along the optical beam path and has an area larger than the cross section of the expanded optical probe beam.

2. The system according to claim 1 wherein the THz sensor distance from the sample is greater than about 20 THz wavelengths.

3. The system according to claim 1 further comprising delay means for delaying a time of arrival of a pulsed THz beam at the THz sensor relative to the arrival of an optical probe beam at the THz sensor.

4. The system according to claim 3 further comprising a controller for controlling a frequency of THz beam pulses relative to a frequency of optical probe beam pulses.

5. The system according to claim 4 further comprising synchronization means for adjusting a data acquisition rate of the sensor relative to the THz beam pulse frequency.

6. The system according to claim 5 further comprising a computer.

7. The system according to claim 6 wherein the computer is programmed for any one or more of the functions of controlling, collecting, storing, and analyzing electrical data generated by the optical sensor.

8. The system according to claim 7 wherein the function of analyzing the data comprises reconstructing an image of the sample using reconstruction algorithms based on the Helmoltz equation.

9. The system according to claim 7 wherein the function of analyzing the data comprises reconstructing an image of the sample using the Fresnel-Kirchhoff reconstruction algorithms.

10. The system according to claim 7 wherein the function of analyzing the data comprises reconstructing an image of the sample using one of the first Born approximation or the first Rytov approximation.

11. The system according to claim 2 wherein the THz sensor is a ZnTe electro-optic crystal.

12. The system according to claim 2 wherein the optical sensor is a CCD sensor.

13. The system according to claim 2 wherein the THz beam comprises THz radiation having a frequency between about 0.1 and 0.5 THz.

14. A method for performing diffraction tomography using terahertz (THz) frequency radiation, the method comprising:
 a. generating a pulsed optical radiation beam and a pulsed THz radiation beam;
 b. expanding and collimating the pulsed THz radiation beam to form a pulsed collimated THz beam traveling along a first path;
 c. transmitting the collimated THz beam through a sample area located in the path;
 d. impinging the transmitted THz collimated beam on a sensor located at a distance from the sample and having an area sufficiently large to intercept all of the collimated THz beam plus all THz radiation diverging at least about 12 degrees from the THz collimated beam, the distance been greater than 20 THz wavelengths from a sample placed in the sample area;
 e. expanding and collimating the optical radiation beam to form a pulsed collimated probe beam having a probe beam area such that when the expanded collimated probe beam impinges on the sensor the probe beam area encompasses the intercepted THz radiation;
 f. impinging the expanded pulsed collimated optical radiation probe beam onto the sensor;
 g. synchronizing the pulsed optical beam and the pulsed THz beam and delaying the arrival of the THz pulses to the sensor relative to the arrival of the probe beam pulses to the sensor by a pre-selected time delay;
 h. detecting and storing a two-dimensional pixel-by-pixel amplitude distribution of the probe beam emerging from the sensor representing a two-dimensional amplitude distribution of the THz beam incident on the sensor;
 i. repeating steps g and h a plurality of times for different time delays to obtain a temporal profile of the two-dimensional THz pulse amplitude distribution;
 j. placing a sample in the sample area in a first orientation relative to the first path and repeating steps c through i to obtain a first orientation temporal profile of the THz pulse amplitude for a plurality of pixels in the collimated probe beam following THz radiation passage through the sample;
 k. repeating steps c through j a plurality of times for a plurality of sample orientations relative to the THz beam to obtain the temporal profile for a plurality of pixels in the probe beam for a plurality of sample orientations; and
 l. reconstructing an image of the sample from the temporal profiles.

15. The method of claim 14 wherein the step of generating the THz beam comprises generating the THz beam having a frequency between about 0.1 and 0.5 THz.

16. The method of claim 15 wherein the step of generating the THz beam comprises generating the THz beam having a frequency between about 0.15 and 0.25 THz.

17. The method according to claim 14 wherein the step of generating the THz beam comprises the step of selecting a frequency for the beam that provides optimum quality for maximum signal-to-noise ratio.

18. The method of claim 14 wherein the step of reconstructing the image comprises numerically transforming the temporal profiles for each pixel for each orientation using a Fourier transformation to obtain a frequency domain THz amplitude.

19. The method of claim 18 wherein the Fourier transformation provides a selection criterion for selecting the generated THz beam frequency.

20. The method of claim 14 wherein the reconstructed image is a three-dimensional rendition of the sample.

21. The method of claim 20 wherein the three-dimensional rendition of the sample comprises applying one of the first Born approximation or the first Rytov approximation.

22. A method for performing diffraction tomography using terahertz (THz) frequency radiation, the method comprising:
 positioning a two-dimensional sensor in a path of an expanded optical probe radiation and an expanded THz radiation, at a distance from a sample such that all THz radiation illuminating the sample and scattered thereby within at least about 12 degrees from a propagation direction of the THz radiation illuminating the sample is intercepted by the sensor;
 adjusting the expanded optical probe beam cross sectional area to encompass all of the THz radiation intercepted by the sensor;
 adjusting the THz radiation frequency to between about 0.15 and 0.5 THz;
 detecting a two-dimensional spatial optical amplitude distribution in the expanded optical probe beam in the absence of a sample and for a plurality of delay times and for a plurality of illumination angles in the presence of the sample; and reconstructing an image of the sample by deriving a two-dimensional time domain amplitude profile for each of the plurality of illuminating angles and applying a reconstruction algorithm.

23. The method of claim 22 wherein the reconstruction algorithm is one of the first Born approximation or the first Rytov approximation.

* * * * *